US00PP25354P2

(12) United States Plant Patent
Pieters

(10) Patent No.: US PP25,354 P2
(45) Date of Patent: Mar. 17, 2015

(54) ***CHRYSANTHEMUM* PLANT NAMED 'RED SAN REMO RUNNER'**

(50) Latin Name: *Chrysanthemum×morifolium*
Varietal Denomination: Red San Remo Runner

(71) Applicant: Luc Remi Johan Pieters, Staden-Oostnieuwkerke (BE)

(72) Inventor: Luc Remi Johan Pieters, Staden-Oostnieuwkerke (BE)

(73) Assignee: Pieters Joseph & Luc B.V.B.A, Staden-Ogtnieuwkerke (BE)

( * ) Notice: Subject to any disclaimer, the term of this patent is extended or adjusted under 35 U.S.C. 154(b) by 136 days.

(21) Appl. No.: 13/815,609

(22) Filed: Mar. 11, 2013

(51) Int. Cl.
*A01H 5/00* (2006.01)

(52) U.S. Cl.
USPC ..... Plt./293

(58) Field of Classification Search
USPC ..... Plt./293
See application file for complete search history.

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'Red San Remo Runner', characterized by its uniform, upright, broadly spreading and mounding plant habit; moderately vigorous to vigorous growth habit; freely branching habit; dense and full plant habit; uniform and freely flowering habit; large decorative-type inflorescences with dark red-colored ray florets; and good garden performance.

2 Drawing Sheets

Botanical designation: *Chrysanthemum×morifolium.*
Cultivar denomination: 'RED SAN REMO RUNNER'.

CROSS-REFERENCED TO CLOSELY-RELATED APPLICATIONS

Title: *Chrysanthemum* Plant Named 'Yellow San Remo Runner'
Applicant: Luc Remi Johan Pieters
Filed: Concurrently with this application U.S. Plant patent application Ser. No. 13/815,611

BACKGROUND OF THE INVENTION

The present invention relates to a new and distinct cultivar of *Chrysanthemum* plant, botanically known as *Chrysanthemum×morifolium* and hereinafter referred to by the name 'Red San Remo Runner'.

The new *Chrysanthemum* plant is a naturally-occurring whole plant mutation of *Chrysanthemum×morifolium* 'Bronze San Remo Runner', disclosed in U.S. Plant Pat. No. 23,319. The new *Chrysanthemum* plant was discovered and selected by the Inventor as a flowering plant from within a population of plants of 'Bronze San Remo Runner' in a controlled greenhouse environment in Staden-Oostnieuwkerke, Belgium in October, 2010.

Asexual reproduction of the new *Chrysanthemum* plant by vegetative cuttings was first conducted in a controlled greenhouse environment in Staden-Oostnieuwkerke, Belgium in January, 2011. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environmental conditions such as temperature, daylength and light intensity, without, however, any variance in genotype.

The following traits have been repeatedly observed and are determined to be the unique characteristics of 'Red San Remo Runner'. These characteristics in combination distinguish 'Red San Remo Runner' as a new and distinct *Chrysanthemum* plant:

1. Uniform, upright, broadly spreading and mounding plant habit; moderately vigorous to vigorous growth habit.
2. Freely branching habit; dense and full plant habit.
3. Uniform and freely flowering habit.
4. Large decorative-type inflorescences with dark red-colored ray florets.
5. Good garden performance.

Plants of the new *Chrysanthemum* differ primarily from the mutation parent, 'Bronze San Remo Runner', in ray floret color as plants of 'Bronze San Remo Runner' have greyed orange-colored ray florets.

Plants of the new *Chrysanthemum* can be compared to plants of *Chrysanthemum×morifolium* 'Yellow San Remo Runner', disclosed in a U.S. Plant patent application Ser. No. 13/815,611 filed concurrently. In side-by-side comparisons conducted in Staden-Oostnieuwkerke, Belgium, plants of the new *Chrysanthemum* differ primarily from plants of 'Yellow San Remo Runner' in ray floret color.

Plants of the new *Chrysanthemum* can also be compared to plants of *Chrysanthemum×morifolium* 'San Remo Runner', not patented. In side-by-side comparisons conducted in Staden-Oostnieuwkerke, Belgium, plants of the new *Chrysanthemum* differed from plants of 'San Remo Runner' primarily in ray floret color as plants of 'San Remo Runner' had pink-colored ray florets.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Red San Remo Runner' grown in a container.

The photograph on the second sheet are close-up views of the upper and lower surfaces of typical inflorescences (left) and upper and lower surfaces of typical leaves (right) of 'Red San Remo Runner'.

DETAILED BOTANICAL DESCRIPTION

The aforementioned photographs and following observations and measurements describe plants grown during the summer and autumn in 17-cm containers in an outdoor nursery in Staden-Oostnieuwkerke, Belgium and under conditions and cultural practices typical of commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Red San Remo Runner'.

Parentage: Naturally-occurring whole plant mutation of *Chrysanthemum×morifolium* 'Bronze San Remo Runner', disclosed in U.S. Plant patent application Ser. No. 13/066,463.

Propagation:

*Type*.—Terminal vegetative cuttings.

*Time to initiate roots, summer*.—About 14 days at temperatures about 20° C.

*Time to initiate roots, winter*.—About 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; light brown in color.

*Rooting habit*.—Freely branching; medium density.

Plant description:

*Plant and growth habit*.—Perennial *Chrysanthemum* plant with decorative type inflorescences; stems upright and broadly spreading giving a uniformly mounding appearance to the plant; very freely branching habit with about 70 lateral branches developing per plant; pinching enhances lateral branch development; dense and full plant habit; moderately vigorous to vigorous growth habit.

*Plant height*.—About 28 cm.

*Plant width*.—About 59.5 cm.

*Lateral branches*.—Length: About 13.1 cm. Diameter: About 3.5 mm. Internode length: About 1.7 cm. Strength: Strong. Aspect: Lateral branches positioned about 55° from the main stem. Texture: Densely pubescent; longitudinally ridged. Color: Close to 177A.

*Leaves*.—Arrangement: Alternate, simple. Length: About 4.4 cm. Width: About 2.4 cm. Shape: Broadly ovate, three to five-lobed Apex: Abruptly acute. Base: Attenuate. Margin: Palmately lobed and coarsely serrate, sinuses convergent to parallel. Texture, upper surface: Moderately pubescent. Texture, lower surface: Densely pubescent. Venation pattern: Pinnate. Color: Developing leaves, upper surface: Close to N137B. Developing leaves, lower surface: Close to 137C and 138A. Fully expanded leaves, upper surface: Close to N137B; venation, close to 146C. Fully expanded leaves, lower surface: Between 137C and 147B; venation, close to 147B. Petioles: Length: About 9 mm. Diameter: About 1 mm by 2 mm. Texture, upper and lower surfaces: Densely pubescent. Color, upper and lower surfaces: Close to 148A.

Inflorescence description:

*Form and arrangement*.—Decorative inflorescence form; inflorescences borne on terminals above foliar plane; disc and ray florets arranged acropetally on a capitulum.

*Fragrance*.—Faintly fragrant, pungent.

*Flowering response*.—Under natural season conditions, plants begin flowering about October 10$^{th}$ in Belgium.

*Postproduction longevity*.—Inflorescences maintain good color and substance for about three weeks in an outdoor nursery; inflorescences not persistent.

*Quantity of inflorescences*.—About 13 inflorescences develop per lateral branch; about 850 inflorescences develop per plant.

*Inflorescence buds*.—Height: About 6 mm. Diameter: About 7 mm. Shape: Flattened globular. Color: Close to 143A; margins of phyllaries, close to 200A.

*Inflorescence diameter*.—About 4.2 cm.

*Inflorescence depth* (*height*).—About 2.3 cm.

*Disc diameter*.—About 6 mm.

*Receptacle diameter*.—About 4 mm.

*Receptacle height*.—About 5 mm.

*Receptacle color*.—Close to 145A to 145B.

*Ray florets*.—Number of ray florets per inflorescence: About 210 arranged in about nine whorls. Length: About 1.8 cm. Width: About 5 mm. Shape: Oblong. Apex: Obtuse. Base: Cuneate. Margin: Entire. Aspect: About 45° from vertical. Texture, upper surface: Smooth, glabrous; velvety; slightly longitudinally ridged. Texture, lower surface: Smooth, glabrous; longitudinally ridged. Color: When opening, upper surface: Between 46A and 180A. When opening, lower surface: Close to 184C. Fully opened, upper surface: Between 53A and 181A to 181B; color becoming closer to 187C with development. Fully opened, lower surface: Close to 185D; color becoming closer to N186D with development.

*Disc florets*.—Number of disc florets per inflorescence: About ten massed at the center of the inflorescence. Length: About 6 mm. Diameter: About 1.5 mm. Shape: Lower 80% fused into a tube; free apices are acute. Texture, inner and outer surfaces: Smooth, glabrous. Color: Towards the apex, close to 12A; midsection and towards the base, close to 1D.

*Phyllaries*.—Number of phyllaries per inflorescence: About 24 arranged in about three whorls. Length: About 7 mm. Width: About 2 mm. Shape: Ovate. Apex: Bluntly acute. Base: Cuneate. Margin: Entire. Texture, upper surface: Smooth, glabrous. Texture, lower surface: Pubescent. Color, upper and lower surfaces: Close to 143A; margins, close to N199A to N1998.

*Peduncles*.—Length, terminal peduncle: About 6.1 cm. Length, fourth peduncle: About 7.2 cm. Length, seventh peduncle: About 7.3 cm. Diameter: About 1.5 mm. Aspect: Erect to about 30° from vertical. Strength: Strong. Texture: Densely pubescent. Color: Close to 148A.

*Reproductive organs*.—Androecium: Present only on disc florets. Number of stamens per floret: Five. Filament length: About 1 mm. Filament color: Close to 150D. Anther length: About 1.2 mm. Anther shape: Narrowly oblong. Anther color: Close to 21A. Pollen amount: Scarce. Pollen color: Close to 13A. Gynoecium: Present on ray and disc florets. Number of pistils per floret: One. Pistil length: About 5 mm. Style length: About 4 mm. Style color: Close to 10A. Stigma shape: Cleft, decurrent. Stigma color: Close to 13A. Ovary color: Close to 145D.

*Seeds and fruits*.—Seed and fruit development have not been observed on plants of the new *Chrysanthemum*.

Disease & pest resistance: Plants of the new *Chrysanthemum* have been observed not to be susceptible to Rust pathogens; resistance to pests and other pathogens common to *Chrysanthemum* plants has not been observed on plants of the new *Chrysanthemum* grown under commercial conditions.

Garden performance: Plants of the new *Chrysanthemum* have good garden performance, are hardy to USDA Hardiness Zones 7 to 8 and tolerate high temperatures of about 35° C.

It is claimed:

1. A new and distinct *Chrysanthemum* plant named 'Red San Remo Runner' as illustrated and described.

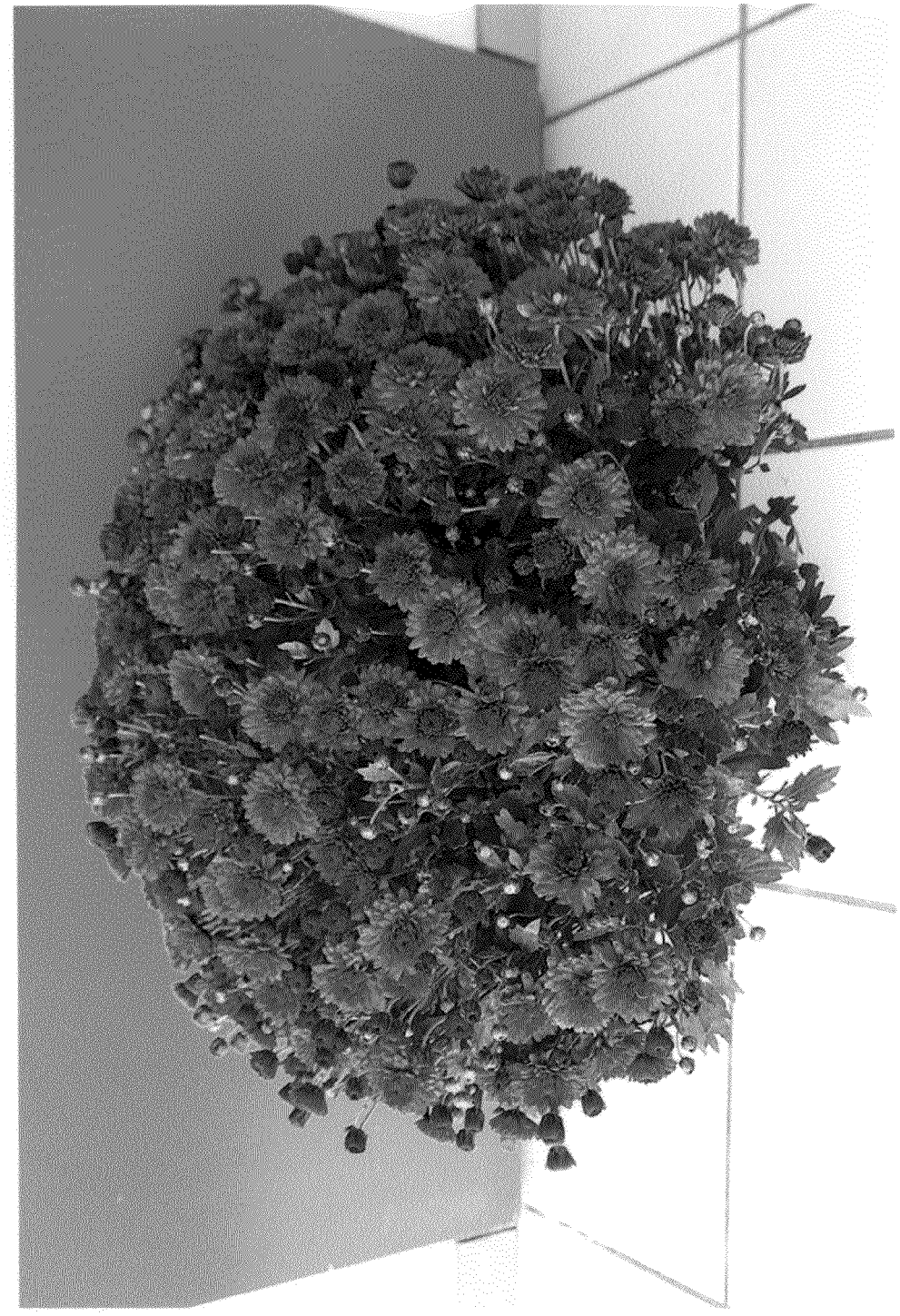

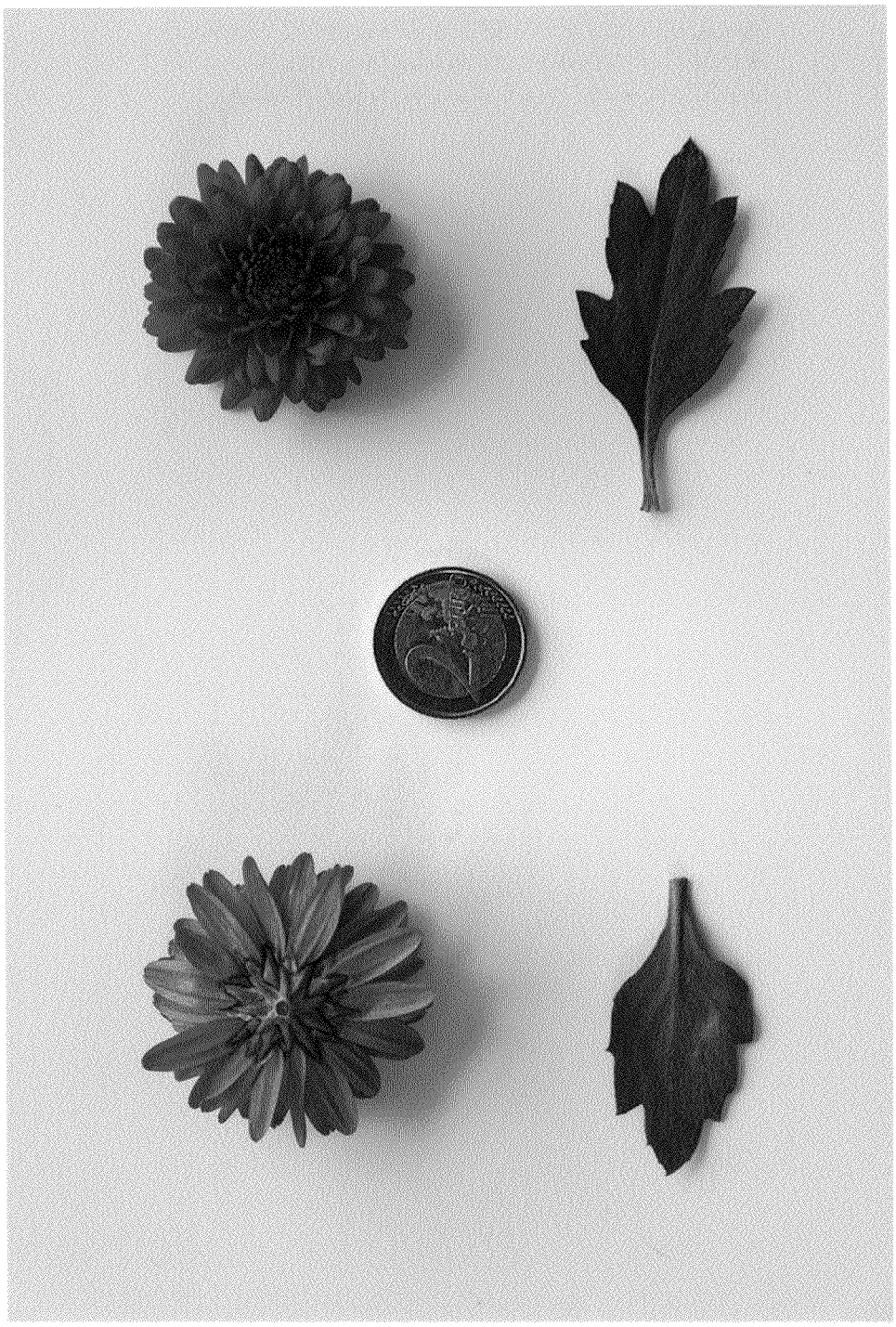

* * * * *